(12) United States Patent
Muller et al.

(10) Patent No.: US 9,085,524 B2
(45) Date of Patent: Jul. 21, 2015

(54) METHOD FOR THE PRODUCTION OF CARBOXYLIC ACID ESTERS DURING A TRANSPORT

(75) Inventors: Heinz Muller, Monheim (DE); Diana Maker, Monheim (DE)

(73) Assignee: Emery Oleochemicals GmbH, Dusseldorf (DE)

( * ) Notice: Subject to any disclaimer, the term of this patent is extended or adjusted under 35 U.S.C. 154(b) by 94 days.

(21) Appl. No.: 13/883,408

(22) PCT Filed: Nov. 7, 2011

(86) PCT No.: PCT/EP2011/069559
§ 371 (c)(1),
(2), (4) Date: Jul. 9, 2013

(87) PCT Pub. No.: WO2012/062709
PCT Pub. Date: May 18, 2012

(65) Prior Publication Data
US 2013/0289290 A1    Oct. 31, 2013

(30) Foreign Application Priority Data
Nov. 11, 2010    (DE) .......................... 10 2010 050 917

(51) Int. Cl.
| C11C 3/00 | (2006.01) |
| C07C 67/08 | (2006.01) |
| C07C 67/03 | (2006.01) |
| B63B 35/44 | (2006.01) |

(52) U.S. Cl.
CPC ................. *C07C 67/08* (2013.01); *C07C 67/03* (2013.01); *B63B 35/44* (2013.01); *B63B 2035/4473* (2013.01)

(58) Field of Classification Search
CPC ........ C07C 67/08; C07C 67/03; C11C 3/003; Y02E 50/13; C10L 1/026
USPC ................................................. 554/124, 170
See application file for complete search history.

(56) References Cited

U.S. PATENT DOCUMENTS

| 5,663,122 A | 9/1997 | Mueller et al. |
| 5,846,601 A | 12/1998 | Ritter et al. |
| 5,869,434 A | 2/1999 | Mueller et al. |
| 6,289,989 B1 | 9/2001 | Mueller et al. |
| 6,350,788 B1 | 2/2002 | Herold et al. |
| 6,716,799 B1 | 4/2004 | Mueller et al. |
| 6,806,235 B1 | 10/2004 | Mueller et al. |
| 7,666,820 B2 | 2/2010 | Mueller et al. |
| 7,741,248 B2 | 6/2010 | Mueller et al. |
| 7,959,743 B2 | 6/2011 | Mueller et al. |
| 8,148,305 B2 | 4/2012 | Westfechtel et al. |
| 8,148,561 B2 | 4/2012 | Ansmann et al. |
| 8,153,562 B2 | 4/2012 | Muller et al. |
| 8,193,125 B2 | 6/2012 | Muller et al. |
| 8,236,735 B2 | 8/2012 | Maker et al. |
| 8,398,942 B2 | 3/2013 | Brasil |
| 2006/0041158 A1 | 2/2006 | Albers et al. |
| 2010/0258307 A1 | 10/2010 | Muller et al. |

FOREIGN PATENT DOCUMENTS

| DE | 10251984 A1 | 5/2004 |
| DE | 102005052173 A1 | 5/2007 |
| WO | 2008047142 A2 | 4/2008 |
| WO | WO 2008047142 A2 * | 4/2008 |
| WO | 2008129415 A2 | 10/2008 |
| WO | 2010085864 A1 | 8/2010 |
| WO | 2010093670 A1 | 8/2010 |

OTHER PUBLICATIONS

German language International Search Report mailed on Jan. 4, 2012 in PCT/EP2011/069559.

* cited by examiner

*Primary Examiner* — Deborah D Carr
(74) *Attorney, Agent, or Firm* — Philp P. McCann; John P. Zimmer; Smith Moore Leatherwood LLP

(57) ABSTRACT

The present invention concerns a method for the production of carboxylic acid esters containing the steps:

a. Supplying of a component containing carboxylic acid and an alcohol;

b. Bringing the component containing carboxylic acid in contact with the alcohol in a container for a conversion to carboxylic acid esters by means of esterification or transesterification, characterized in that the container is moved over a distance of at least 1 kilometer during the esterification or the transesterification.

The present invention also concerns the use of a ship.

16 Claims, No Drawings

METHOD FOR THE PRODUCTION OF CARBOXYLIC ACID ESTERS DURING A TRANSPORT

This application is a national stage application under 35 U.S.C. 371 of International Application No. PCT/EP2011/069559 filed 7 Nov. 2011, which claims priority to German Application No. DE 10 2010 050 917.5 filed 11 Nov. 2010, the disclosures of which are expressly incorporated herein by reference.

FIELD

The present invention concerns a method for the production of carboxylic acid esters, which are to be obtained by means of esterification or transesterification from components containing carboxylic acids and alcohols. The invention also concerns the use of a ship.

BACKGROUND

Carboxylic acid esters are used widely in technology. Exemplary uses lie in the field of lubricants and the substrates for cosmetics. Thus, DE 10 2005 052 173 A1 discloses the use of fatty acid-2-ethylhexyl ester mixtures as the oil components in cosmetic and pharmaceutical products.

Numerous methods are known for obtaining carboxylic esters from components containing carboxylic acids, and alcohols. Common to all of these methods is that components containing carboxylic acids, and alcohol are transported separately to the location for the technical esterification or transesterification, and are first brought into contact with one another at the location where the technical esterification is to be carried out. For this in particular, the step of the transshipment of the components containing carboxylic acids is problematic due to its frequently high degree of viscosity, which in typical methods must be carried out at least twice.

With some components containing carboxylic acids having a high melting temperature, a melting is required prior to the transshipment or conversion, as a result of which, the expenditures for this step increase. Examples of such components containing carboxylic acids are pure carboxylic acids such as oxalic acid, which tends to decompose during the melting process, fumaric acid, salicylic acid, palmitic acid, heptadecanoic acid, stearic acid, and arachidic acid, the melting point of which is above 50° C. Long chain carboxylic acids having polyvalent alcohols also exist in the solid state at room temperature. By way of example, at this point glycerin trilaurate, having a melting temperature of 46.5° C., is referenced.

Another disadvantage of this two-step method (first step: separate transport of the reactants to the place of esterification, second step: bringing the reactants into contact with one another at the place of esterification) is the result of the low reaction rate of the esterification or transesterification reactions. In order to counteract the kinetics of the reaction, and to obtain reasonable dwell times in the processing facilities, the esterification or transesterification is carried out in currently customary methods at high temperatures, and accelerated through the use of catalysts. By way of example, a method taken from DE 102 51 984 A1 is referenced at this point, which provides for a conversion at 190-240° C. in the presence of a tetra-alkyl titanate catalyst in 18 hours. Lower temperatures result in significantly longer dwell times, which cannot be tolerated in conventional processing facilities.

SUMMARY

The present invention includes various embodiments as set forth herein.

The present invention assumes the objective of overcoming the disadvantages resulting in the prior art in connection with the production of carboxylic acid esters from a component containing carboxylic acid and an alcohol by means of esterification or transesterification.

DETAILED DESCRIPTION

In particular, the present invention assumes the objective of designing the entire method procedure, starting from the transportation of the reactants all the way through the conversion thereof, such that it is more efficient.

One contribution to the attaining of the tasks specified in the introduction therefore provides a method for the production of carboxylic acid esters containing the steps:

a. Supplying of a component containing carboxylic acid and an alcohol;

b. Bringing of the component containing carboxylic acid and the alcohol into contact with one another in a container for a conversion to carboxylic acid esters by means of esterification or transesterification, characterized in that the container is moved over a distance of at least one kilometer during the esterification or transesterification.

Surprisingly, it has been shown that the objective specified above can be attained by means of combining the transport and conversion steps to form a single-step method. In particular, the handling of such components containing carboxylic acids, which, at room temperature (20° C.), are present in a solid state or in a highly viscous liquid, by means of esterification or transesterification during the transport, can be significantly improved. Positive effects have been observed, in particular with components containing carboxylic acids having a melting temperature above 10° C., or above 20° C. as well, and likewise, above 30° C. The fluidity or pumpability is already increased by at least 10% with a partial conversion, with respect to the quantity of the components containing carboxylic acids. The mode of action is dependent thereby on the precise configuration of the components containing the carboxylic acids.

Carboxylic acid esters are known compounds, per se, which, aside from the method according to the invention, can be produced, in accordance with the known methods of synthetic chemistry, from components containing carboxylic acids and alcohols. If the components containing carboxylic acids concern a pure carboxylic acid, then this conversion is referred to as "esterification." If the components containing carboxylic acids are, however, a compound, which, aside from carboxylic acids, also contains, if applicable, carboxylic acid esters, then aside from the esterification, a "transesterification" can also occur.

In step a. of the method according to the invention, a component containing a carboxylic acid and an alcohol are supplied.

If an ester of a polyvalent alcohol having two or more carboxylic acids is used as the component containing carboxylic acid, then this ester is split during a transesterification, and a carboxylic acid ester is obtained, consisting of the carboxylic acid of the component containing carboxylic acid and the alcohol that is used. If the alcohol that is used is a monovalent alcohol, then the size of the molecule, and thus the melting temperature and viscosity, is reduced by means of this process.

If an ester of a monovalent alcohol having a carboxylic acid is used as the component containing carboxylic acid, then with a transesterification, the alcohol can be replaced in such a manner that the chain length and/or polarity are reduced. This decreases the melting temperature and viscosity.

In an embodiment according to the invention, a pure carboxylic acid, or a mixture thereof with other carboxylic acids, is used as the component containing carboxylic acid. The carboxylic acid mixtures are usually of qualities that can be readily and inexpensively obtained. Examples thereof are C14 and C18 carboxylic acids, preferably having a portion of said carboxylic acids amounting to more than 60% by weight, and preferably more than 70% by weight of a carboxylic acid mixture. For this, for example, split fatty acids from coconut, palm kernel, and palm oils are to be considered. Because the carboxylic acid esters exhibit reduced melting temperatures and viscosities in relation to the constituent carboxylic acids, an esterification reaction also renders the handling thereof easier in comparison with the carboxylic acids. For this, linear and branched, saturated and unsaturated carboxylic acids having 7 to 30 carbon atoms are preferred.

Fatty acids, in particular, are to be considered for the carboxylic acids. For this, hexanoic acid, caprylic acid, nonanoic acid, 2-ethylhexanoic acid, decanoic acid, lauric acid, isotridecylic acid, myristic acid, palmitic acid, palmoleic acid, heptadecanoic acid, stearic acid, isostearic acid, oleic acid, elaidic acid, petroselinic acid, linoleic acid, linolenic acid, eleostearic acid, arachidic acid, gadoleic acid, behenic acid, lignoceric acid, cerotic acid, montanic acid, melissic acid, and erucic acid, or at least two thereof and their technical mixtures, are specified here as preferred. Those fatty acids having 12-18 carbon atoms are particularly preferred.

In step a. a monovalent alcohol is preferably used as the alcohol, wherein said alcohol preferably exhibits 1-16 carbon atoms, particularly preferred is 2-12 carbon atoms, and most preferred is 4-8 carbon atoms. In particular, methanol, 1-propanol, 2-propanol, 1-butanol, 2-butanol, tert-butyl alcohol, propylheptyl alcohol, isotridecyl alcohol, linear-C6, -C8, -C10 alcohols, and ethylhexyl alcohol, as well as mixtures of at least two thereof, are specified as examples of suitable alcohols in accordance with the invention.

In step b. of the method according to the invention, the components containing carboxylic acids and the alcohol are brought into contact with one another in a container for a conversion to the carboxylic acid esters by means of esterification or transesterification, wherein the container is moved over the course of a distance of at least one kilometer during the esterification or transesterification.

All containers suitable for containing components containing carboxylic acids, alcohols and carboxylic acid esters may be considered for the container in which the components containing carboxylic acids and alcohol are to be brought into contact with one another. Typically, containers or barrels made of stainless steel are used for these types of liquids, or solids that can be melted. It is, however, likewise possible to use plastic containers, frequently made of polyethylene, polypropylene, or polyester, or a mixture of at least two thereof.

The movement of the container serves the purpose of transporting the components containing carboxylic acids from the production location or place of purchase (A), to the location (B) at which they will be added to the reactants for some purpose, in the form of a carboxylic acid ester, or as a mixture of carboxylic acid esters. For this purpose, therefore, movements connect the locations A and B in a nearly linear manner, taking into consideration geographical, infrastructural, and other conditions.

In one embodiment according to the invention, the container is moved by means of a ship. Through the use of the transportation period for the conversion of components containing carboxylic acids and alcohol, long reaction times and thus low reaction temperatures in the range of 35-65° C. can be tolerated. This enables the use of alternative methods for heating the container. Those designs which enable the use of the waste heat from a ship's motors for heating the reaction container are thus preferred. These can, for example, be obtained through a positioning of the container in the spatial proximity of a ship's motor, or through the conducting of the heat generated by a ship's motor to the container through the use of a heat-conducting liquid.

Furthermore, such designs in which the reaction container is already heated by means of the climatic conditions during the movement are preferred. This is obtained in that the reaction container is moved in regions having higher air temperatures and/or greater exposure to sunlight. These conditions can be found, for example, in regions having a tropical climate located between the Tropic of Capricorn and the Tropic of Cancer.

The time frame in which the container is moved, or the distance through which it is moved, are not limited per se. Carboxylic acid esters are stable chemical compounds, needing no direct treatment or further processing subsequent to their production. Those designs in which the container is moved for at least three, preferably at least seven, days, or at least over a distance of 100 km, preferably 500 km and particularly preferably 1,500 km, and particularly preferably 5,000 km, are preferred.

In one embodiment according to the invention, components containing carboxylic acids and alcohol are used in technically typical purities. The water content in the reaction mixture should therefore not exceed 10% by weight, with respect to the reaction mixture.

Due to the tolerability of longer reaction times, the use of catalysts, as is otherwise typical in the production of carboxylic acid esters, can be reduced to less than 20% by weight of catalyst, with respect to the reaction mixture.

One contribution to attaining the objective specified in the introduction also provides for the use of a ship as the location of the production of a carboxylic acid ester by means of bringing a component containing carboxylic acid in contact with an alcohol in a container located on the ship, wherein the bringing into contact, and thus the esterification or transesterification, preferably occurs during the travel of the ship.

The invention shall now be explained in greater detail based on examples, which do not represent a limitation to the invention.

EXAMPLE

A method according to the invention is used for the conversion of a fatty acid mixture with ethylhexyl alcohol. The fatty acid mixture has a large portion of oleic acid, and at room temperature is a turbid, viscous liquid with sediment. 2 kg of the fatty acid mixture are added to 0.5 kg ethylhexyl alcohol, and moved for four weeks at 40° C. without actively reinforcing the mixing thereof by means of an agitator. The conversion of the carboxylic acid is quantified by the acid value.

| Time [Weeks] | Acid Value [mg KOH/g] | Viscosity |
|---|---|---|
| 0 | 144.3 | High, with sediment |
| 2 | 78.0 | High |
| 4 | 68.8 | Medium |

This shows that 68.8% of the carboxylic acid is converted with respect to the quantity of carboxylic acid. As a result of the esterification, the viscosity is reduced and the sediment is dissolved.

What is claimed is:

1. A method for the production of carboxylic acid esters comprising the steps:
   a. supplying a component containing a carboxylic acid and an alcohol; and
   b. bringing the component containing a carboxylic acid into contact with the alcohol in a container to provide a reaction mixture for a conversion to carboxylic acid esters by means of esterification or transesterification, wherein the reaction mixture has a temperature in the range of from 35° C. to 65° C.; and
   c. moving the container over a distance of at least 1 kilometer and for at least seven days during the esterification or the transesterification.

2. The method according to claim 1, wherein the melting temperature of the component containing a carboxylic acid is above 10° C.

3. The method according to claim 1, wherein the alcohol comprises a monovalent alcohol.

4. The method according to claim 1, wherein the component containing a carboxylic acid is a carboxylic acid.

5. The method according to claim 4, wherein the carboxylic acid is a carboxylic acid having 7-30 carbon atoms.

6. The method according to claim 4, wherein a fatty acid is used as the carboxylic acid.

7. The method according to claim 6, wherein the fatty acid contains 12-18 carbon atoms.

8. The method according to claim 1, wherein the movement of the container occurs by a ship.

9. The method according to claim 1, wherein the reaction mixture is heated by a ship's motor.

10. The method according to claim 1, wherein the container is heated by climate conditions in the course of the movement.

11. The method according to claim 1, wherein the container is moved during the esterification over a distance of at least 100 km, preferably over a distance of at least 500 km, and particularly preferably over a distance of at least 1,500 km.

12. The method according to claim 1, wherein conversion of at least 10% occurs, with respect to the quantity of the component containing a carboxylic acid.

13. The method according to claim 1, wherein the movement occurs at a relative air humidity in a range of 10-100%.

14. The method according to claim 1, wherein the portion of water in the reaction mixture does not exceed 10% by weight, with respect to the reaction mixture.

15. The method according to claim 1, wherein the conversion occurs with less than 20% by weight of a catalyst, with respect to the reaction mixture.

16. The method according to claim 1, wherein the container is moved during the esterification over a distance of at least 1,500 km.

* * * * *